(12) United States Patent
Trieu

(10) Patent No.: US 8,277,508 B2
(45) Date of Patent: Oct. 2, 2012

(54) HYBRID INTERVERTEBRAL DISC SYSTEM

(75) Inventor: Hai H. Trieu, Cordova, TN (US)

(73) Assignee: Warsaw Orthopedic, Warsaw, IN (US)

( * ) Notice: Subject to any disclaimer, the term of this patent is extended or adjusted under 35 U.S.C. 154(b) by 1253 days.

(21) Appl. No.: 11/487,841

(22) Filed: Jul. 17, 2006

(65) Prior Publication Data

US 2006/0259144 A1 Nov. 16, 2006

Related U.S. Application Data

(62) Division of application No. 10/765,260, filed on Jan. 27, 2004, now Pat. No. 7,250,060.

(51) Int. Cl.
*A61F 2/44* (2006.01)

(52) U.S. Cl. .................... 623/17.15; 623/17.16

(58) Field of Classification Search ..... 623/17.11–17.16
See application file for complete search history.

(56) References Cited

U.S. PATENT DOCUMENTS

| | | | |
|---|---|---|---|
| 4,759,769 A | 7/1988 | Hedman et al. | |
| 4,911,718 A | 3/1990 | Lee et al. | |
| 4,932,969 A | 6/1990 | Frey et al. | |
| 5,071,437 A | 12/1991 | Steffee | |
| 5,314,477 A | 5/1994 | Marnay | |
| 5,370,697 A * | 12/1994 | Baumgartner | 623/17.15 |
| 5,401,269 A | 3/1995 | Buttner-Janz | |
| 5,545,229 A | 8/1996 | Parsons et al. | |
| 5,674,294 A | 10/1997 | Bainville et al. | |
| 5,702,450 A | 12/1997 | Bisserie | |
| 5,824,094 A | 10/1998 | Serhan et al. | |
| 5,893,889 A | 4/1999 | Harrington | |
| 6,348,071 B1 | 2/2002 | Steffee et al. | |
| 6,352,556 B1 | 3/2002 | Kretschmer et al. | |
| 6,402,785 B1 | 6/2002 | Zdeblick et al. | |
| 6,520,996 B1 | 2/2003 | Manasas et al. | |
| 6,592,624 B1 | 7/2003 | Fraser et al. | |
| 6,607,558 B2 | 8/2003 | Kuras | |
| 6,607,559 B2 | 8/2003 | Ralph et al. | |
| 6,626,943 B2 | 9/2003 | Eberlein et al. | |

(Continued)

FOREIGN PATENT DOCUMENTS

| | | |
|---|---|---|
| EP | 0517030 | 5/1992 |
| EP | 0 566 810 | 10/1993 |
| FR | 2 787 014 | 6/2000 |
| FR | 2 787 021 | 6/2000 |
| WO | WO 00/13619 | 3/2000 |
| WO | WO 00/53127 | 9/2000 |
| WO | WO 01/64142 | 9/2001 |
| WO | WO 03/094806 | 11/2003 |

OTHER PUBLICATIONS

Patent Cooperation Treaty—European Patent Office, "Notification of Transmittal of The International Search Report and The Written Opinion of the International Searching Authority, or the Declaration," May 2, 2005, 14 pages.

*Primary Examiner* — Eduardo C Robert
*Assistant Examiner* — Stuart S Bray

(57) ABSTRACT

An intervertebral disc prosthesis is adapted for implantation between first and second vertebral endplates. The prosthesis comprises a first endplate assembly for engaging the first vertebral endplate. The first endplate assembly has a concave first inner surface. The prosthesis further comprises a second endplate assembly for engaging the second vertebral endplate. The second endplate assembly has a concave second inner surface. The prosthesis further comprises a core component extending between the first and second inner surfaces and adapted to move relative to the concave first and second inner surfaces. The core component includes a flexible body extending between first and second end surfaces such that the end surfaces are not contiguous. The first and second end surfaces have a hardness greater than the flexible body.

26 Claims, 6 Drawing Sheets

U.S. PATENT DOCUMENTS

| | | | |
|---|---|---|---|
| 6,966,931 B2* | 11/2005 | Huang | 623/17.16 |
| 7,255,714 B2* | 8/2007 | Malek | 623/17.15 |
| 7,601,174 B2* | 10/2009 | Kelly et al. | 623/17.13 |
| 2002/0035400 A1* | 3/2002 | Bryan et al. | 623/17.15 |
| 2003/0135277 A1 | 7/2003 | Bryan et al. | |
| 2003/0187506 A1* | 10/2003 | Ross et al. | 623/17.13 |
| 2003/0204271 A1 | 10/2003 | Ferree | |
| 2004/0002761 A1 | 1/2004 | Rogers et al. | |
| 2004/0002762 A1 | 1/2004 | Hawkins | |
| 2004/0054411 A1* | 3/2004 | Kelly et al. | 623/17.13 |
| 2005/0021145 A1* | 1/2005 | de Villiers et al. | 623/17.14 |

* cited by examiner

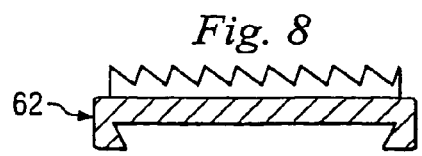
Fig. 8
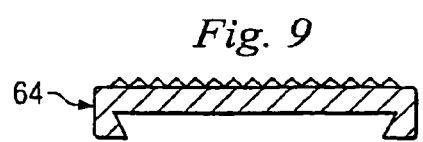
Fig. 9
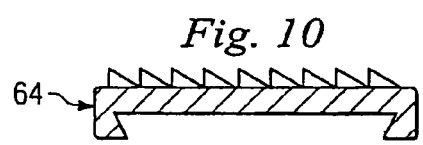
Fig. 10
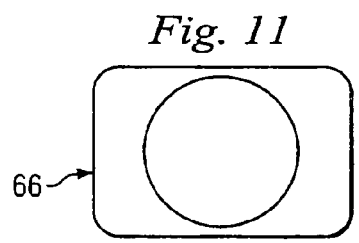
Fig. 11
Fig. 12
Fig. 13
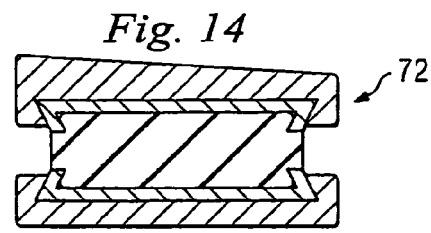
Fig. 14
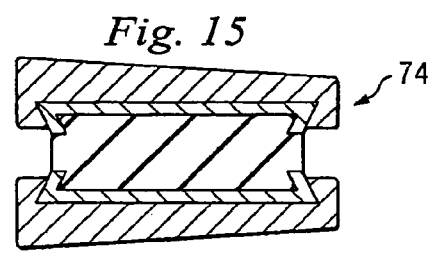
Fig. 15
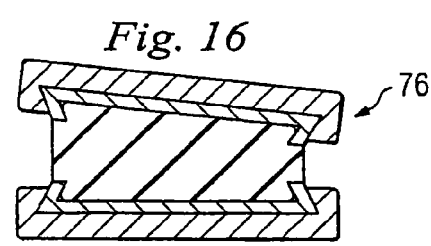
Fig. 16
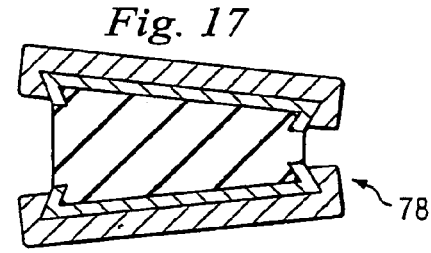
Fig. 17
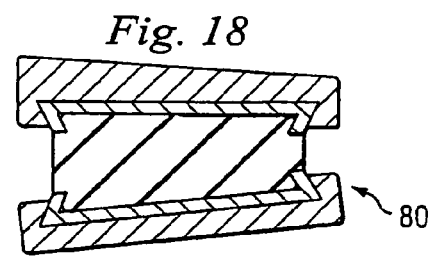
Fig. 18

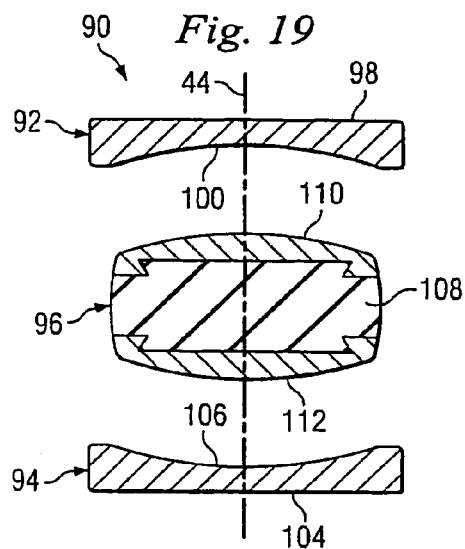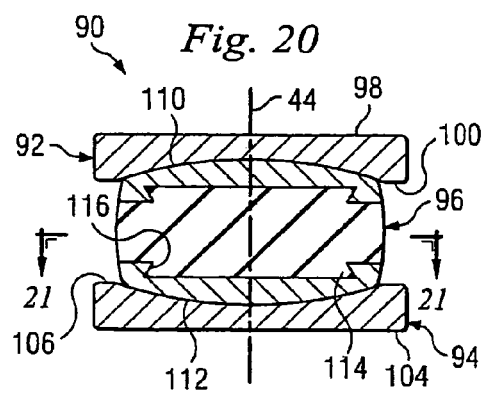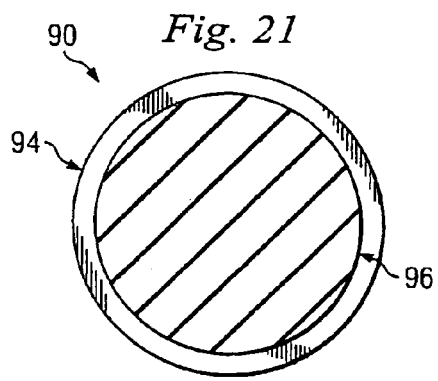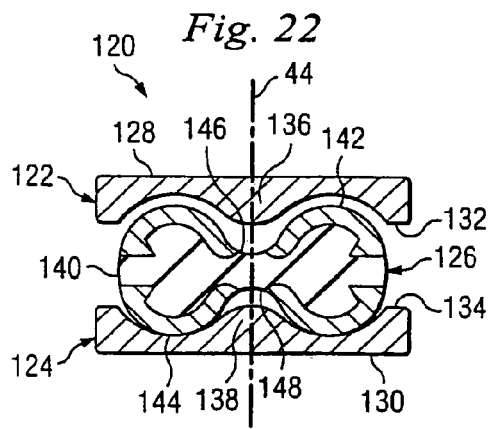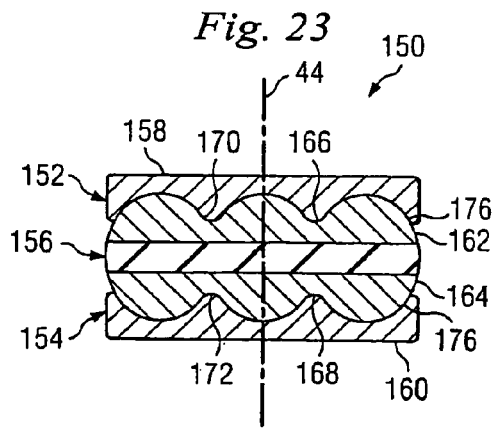

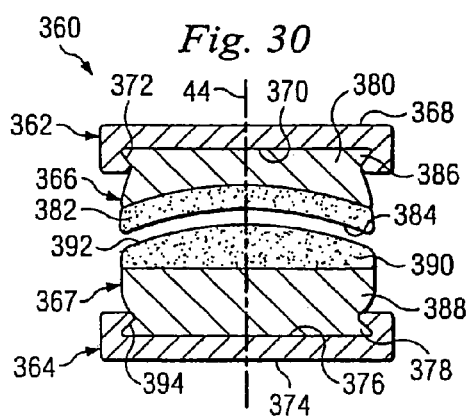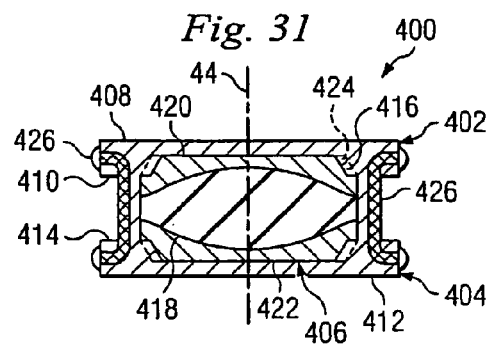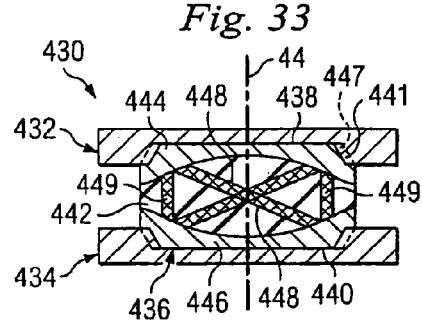

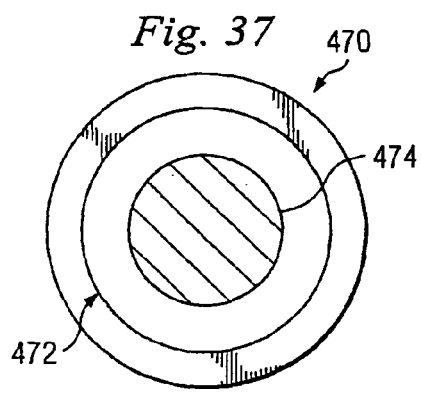
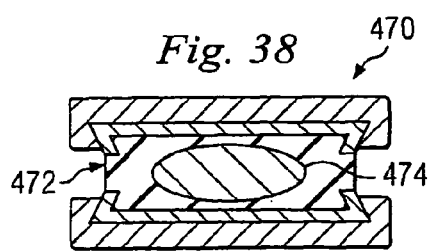
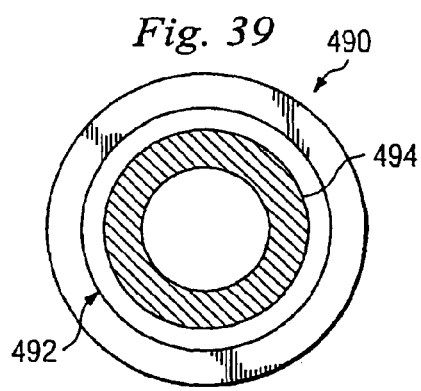
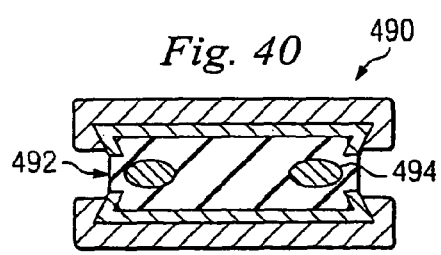
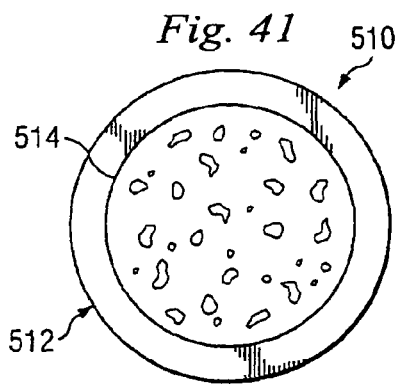
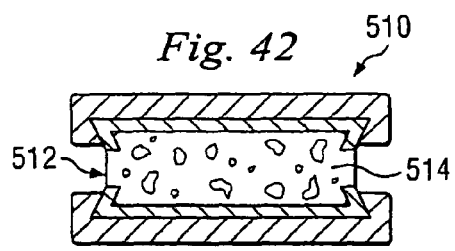

HYBRID INTERVERTEBRAL DISC SYSTEM

CROSS-REFERENCE

This application is a divisional of U.S. patent application Ser. No. 10/765,260, filed Jan. 27, 2004, and is hereby incorporated by reference in its entirety.

BACKGROUND

During the past thirty years, technical advances in the design of large joint reconstructive devices has revolutionized the treatment of degenerative joint disease, moving the standard of care from arthrodesis to arthroplasty. Progress in the treatment of vertebral disc disease, however, has come at a slower pace. Currently, the standard treatment for disc disease remains discectomy followed by vertebral fusion. While this approach may alleviate a patient's present symptoms, accelerated degeneration of adjacent discs is a frequent consequence of the increased motion and forces induced by fusion. Thus, reconstructing the degenerated intervertebral disc with a functional disc prosthesis to provide motion and to reduce deterioration of the adjacent discs may be a more desirable treatment option for many patients.

SUMMARY

In one embodiment, an intervertebral disc prosthesis is adapted for implantation between first and second vertebral endplates. The prosthesis comprises a first endplate assembly for engaging the first vertebral endplate. The first endplate assembly has a concave first inner surface. The prosthesis further comprises a second endplate assembly for engaging the second vertebral endplate. The second endplate assembly has a concave second inner surface. The prosthesis further comprises a core component extending between the first and second inner surfaces and adapted to move relative to the concave first and second inner surfaces. The core component includes a flexible body extending between first and second end surfaces such that the end surfaces are not contiguous. The first and second end surfaces have a hardness greater than the flexible body.

In another embodiment, an intervertebral disc prosthesis comprises a flexible core component including a flexible body and first and second end surfaces separated by a perimeter surface of the flexible body. The prosthesis further comprises first and second endplate portions adapted for articulating contact with the first and second end surfaces, respectively. The first and second end surfaces are more rigid than the flexible body portion.

BRIEF DESCRIPTION OF THE DRAWINGS

FIG. 8 is a side view of an endplate portion of an intervertebral disc prosthesis.

FIG. 9 is an anterior view of an endplate portion of an intervertebral disc prosthesis.

FIG. 10 is a side view of an endplate portion of an intervertebral disc prosthesis.

FIGS. 11-13 are cross sectional top views of intervertebral disc prostheses according to alternative embodiments of the present disclosure.

FIGS. 14-18 are cross sectional side views of intervertebral disc prostheses according to alternative embodiments of the present disclosure.

FIG. 19 is a cross sectional side view of an exploded intervertebral disc prosthesis according to an alternative embodiment of the present disclosure.

FIG. 20 is a cross sectional side view of an assembled intervertebral disc prosthesis according to the embodiment of FIG. 19.

FIG. 21 is a cross sectional top view of an intervertebral disc prosthesis according to the embodiment of FIG. 19.

FIGS. 22-30 are cross sectional side views of assembled intervertebral disc prostheses according to alternative embodiments of the present disclosure.

FIG. 31 is a cross sectional side view of an intervertebral disc prosthesis according to an alternative embodiment of the present invention.

FIG. 32 is a cross sectional top view of an intervertebral disc prosthesis according to the embodiment of FIG. 31.

FIG. 33 is a cross sectional side view of an intervertebral disc prosthesis according to an alternative embodiment of the present invention.

FIG. 34 is a cross sectional top view of an intervertebral disc prosthesis according to the embodiment of FIG. 34.

FIGS. 35, 37, 39, and 41 are cross sectional top views of intervertebral disc prostheses according to alternative embodiments of the present invention.

FIGS. 36, 38, 40, and 42 are cross sectional side views of the intervertebral disc prostheses of the embodiments of FIGS. 35, 37, 39, and 41, respectively.

DETAILED DESCRIPTION

Figure 1:
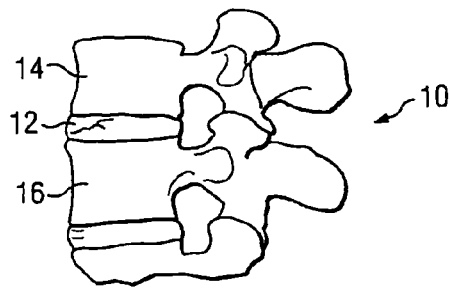
FIG. 1 is a sagittal view of vertebral column having a destroyed disc.

The present invention relates generally to vertebral reconstructive devices, and more particularly, to a functional intervertebral disc prosthesis. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a vertebral column with a damaged intervertebral disc 12 extending between two intact vertebrae 14 and 16. In a typical surgical discectomy, the damaged disc 12 is removed creating a void between the two intact vertebrae 14 and 16. This procedure may be performed using an anterior, anterolateral, lateral, or other approach known to one skilled in the art.

Figure 2:
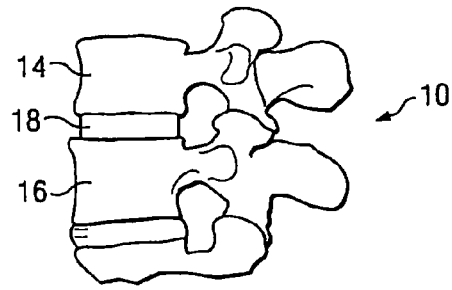
FIG. 2 is a sagittal view of vertebral column with an intervertebral prosthesis replacing the destroyed disc.

Referring now to FIG. 2, a prosthesis 18 may be provided to fill the void between the vertebrae 14 and 16.

Figure 3:
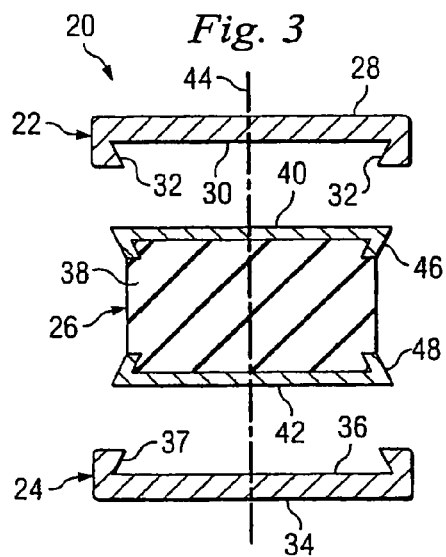
FIG. 3 is a cross sectional side view of an exploded intervertebral disc prosthesis according to a first embodiment of the present disclosure.
Figure 4:
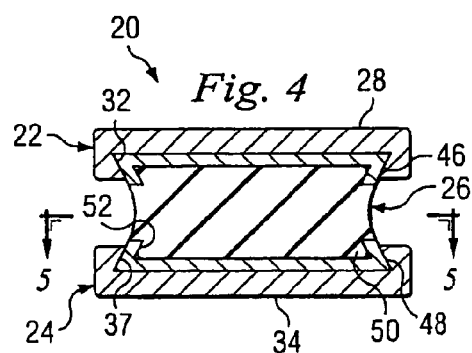
FIG. 4 is a cross sectional side view of an assembled intervertebral disc prosthesis according to the first embodiment of the present disclosure.
Figure 5:
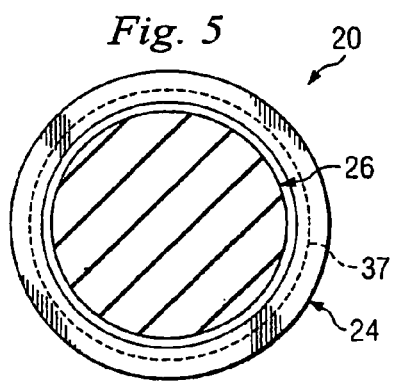
FIG. 5 is a cross sectional top view of the intervertebral disc prosthesis according to the first embodiment of the present disclosure.

Referring now to FIGS. 3-5, an intervertebral disc prosthesis 20 may be used as the prosthesis 18 of FIG. 2. The intervertebral disc prosthesis 20, according to an embodiment of the present invention, includes endplate assemblies 22, 24 and a core component 26. The endplate assembly 22 may include an exterior surface 28 and an interior surface 30. In this embodiment, the surface 30 may be relatively flat and smooth and may have a mirror surface finish. The surface 30 may further include a groove 32. The endplate assembly 24 may have an exterior surface 34 and an interior surface 36. The surface 36 may be relatively flat and smooth and may have a mirror surface finish. The surface 36 may further include a coupling mechanism 37 such as a groove. The articulating interior surfaces 30, 36 may be flat with a mirror finish as shown in this embodiment, however in alternative embodiments, the articulating surfaces may include grooves, dimples or other features to improve lubrication and reduce friction and wear. These surfaces may be treated with any of various techniques to improve wear resistance such as ion-implantation, diamond or diamond-like coating, or other methods that make the surface harder than the original surface.

The core component 26 may include a flexible body 38 having end surfaces 40 and 42. As shown in FIG. 5, the core component 26 may have a generally circular cross-section as viewed from a plane perpendicular to a longitudinal axis 44 (FIG. 3). Alternate cross-sectional shapes may be desirable, and in a single core component 26, the cross sectional shape may vary depending upon the location of the perpendicular plane. In this embodiment, the end surfaces 40 and 42 may be relatively flat and parallel and may incorporate coupling mechanisms 46, 48, respectively which may be ridges. The end surfaces 40, 42 may be integral with the flexible body 38 or may be mechanically or adhesively attached to the flexible body 38. For example, as shown in FIG. 4, a coupling mechanism 50, such as a ridge, formed on the flexible body 38 may engage a coupling mechanism 52, such as a groove, formed on the end surface 42. In alternative embodiments, the core component may have curved end surfaces or end surfaces angled with respect to one another.

The endplate assemblies 22, 24 may be formed of any suitable biocompatible material including metals such as cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

Figure 6:
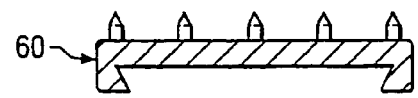
FIG. 6 is a side view of an endplate portion of an intervertebral disc prosthesis.
Figure 7:
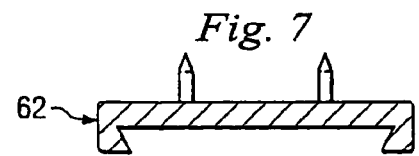
FIG. 7 is an anterior view of an endplate portion of an intervertebral disc prosthesis.

The exterior surfaces 28, 34 may include features or coatings (not shown) which enhance the fixation of the implanted prosthesis. For example, the surfaces may be roughened such as by chemical etching, bead-blasting, sanding, grinding, serrating, and/or diamond-cutting. All or a portion of the exterior surfaces 28, 34 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes as shown on the endplate assembly 60 in FIG. 6 for initial fixation; ridges or keels as shown on the endplate assembly 62 in FIGS. 7 and 8 to prevent migration in the lateral and anterior direction, for example; serrations or diamond cut surfaces as shown on the endplate assembly 64 in FIGS. 9 and 10; fins; posts; and/or other surface textures.

Referring again to FIGS. 3-5, flexible body 38 may be formed from one or more resilient materials which may have a lower modulus than the endplate materials. Suitable materials may include polymeric elastomers such as polyolefin rubbers; polyurethanes (including polyetherurethane, polycarbonate urethane, and polyurethane with or without surface modified endgroups); copolymers of silicone and polyurethane with or without surface modified endgroups; silicones; and hydrogels. Polyisobutylene rubber, polyisoprene rubber, neoprene rubber, nitrile rubber, and/or vulcanized rubber of 5-methyl-1,4-hexadiene may also be suitable.

The core component end surfaces 40, 42 may be modified, treated, coated or lined to enhance the wear resistant and articulating properties of the core component 26. These wear resistant and articulation properties may be provided by cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may be suitable. Polymer materials may also be used including any member of the PAEK family such as PEEK, carbon-reinforced PAEK, or PEKK; polysulfone; polyetherimide; polyimide; UHMWPE; and/or cross-linked UHMWPE. Polyolefin rubbers, polyurethanes, copolymers of silicone and polyurethane, and hydrogels may also provide wear resistance and articulation properties. Wear resistant characteristics may also or alternatively be provided to the end surfaces 40, 42 by modifications such as cross-linking and metal ion implantation.

Although the embodiments of FIGS. 3-5 describe circular endplate assemblies, FIG. 11 shows a rectangular endplate assembly 66. FIG. 12 shows a rectangular endplate assembly 68 with curved sides. FIG. 13 shows a kidney or heart shaped endplate assembly 70. Other endplate geometries may be square, oval, triangular, hexagonal, or any other shape. As shown in the cross sectional top view of FIG. 5, the geometry of the core component may be round, oval, or any other shape which promotes constraint or articulation.

In the embodiment of FIGS. 3-5, the exterior surfaces 28 and 34 may be relatively parallel, but in other embodiments, the surfaces may be angled with respect to each other to accommodate a particular lordotic or kyphotic angle. As shown in FIGS. 14-18, protheses may be tapered, angled, or wedge shaped to achieve a desired lordotic or kyphotic angle. Such angles may be created by incorporating angled endplate assemblies and/or core components. The prosthesis 72 of FIG. 14 is angled by incorporating an angled endplate. The prosthesis 74 of FIG. 15 is angled by incorporating two angled endplates. The prosthesis 76 of FIG. 16 is angled by incorporating flat endplates with a core component having one angled side. The prosthesis 78 of FIG. 17 is angled by incorporating flat endplates with a core component having two angled sides. The prosthesis 80 of FIG. 18 is angled by incorporating an angled endplate and a core component having an angled side.

Referring again to FIG. 4, the prosthesis 20 may be assembled by engaging the ridges 46, 48 of the core component 26 with the grooves 32, 37, respectively of the endplate assemblies. The assembled prosthesis 20 may be implanted into the vertebral column 10 (FIG. 1) in the void created by the removed disc 12 such that the exterior surface 28 engages an endplate of the vertebral body 14 and the exterior surface 34 engages an endplate of the vertebral body 16.

In operation, the prosthesis 20 may elastically deform under compressive loads parallel to the longitudinal axis 44 and may elastically stretch in response to a force which may pull the endplate assemblies away from one another along the longitudinal axis 44. The prosthesis 20 may also deform or flex under flexion-extension or lateral bending motion. The core component 26 may allow a variable center of rotation to permit flexion-extension and lateral bending motions. The flexible nature of the core component 26 may also reduce wear caused by cross-shearing or by articulation in flexion-extension and lateral bending motions. The core component 26 may also flex to permit anterior-posterior or lateral translational displacement of the endplate assembly 22 relative to the endplate assembly 24. Further, as the interface between the end surfaces 40, 42 and the interior surfaces 30, 36, respectively may be rotationally unconstrained, the core component 26 may pivot or rotate about the longitudinal axis 44. The interface may, however, constrain translational movement at the interface. The end plate assemblies 22, 24 may also rotate relative to one another. In alternative embodiments, at least one of the interfaces between the end surfaces 40, 42, and the interior surfaces 30, 36, respectively may permit no rotational or pivotal movement. The engagement of the coupling mechanisms 46, 48 of the core component 26 with the coupling mechanisms 32, 37 may prevent ejection of the core component 26 while permitting rotation of the endplate assemblies 22, 24 relative to the core component.

Referring now to FIGS. 19-21, an intervertebral disc prosthesis 90 may be used as the prosthesis 18 of FIG. 2. The intervertebral disc prosthesis 90, according to an embodiment of the present invention, includes endplate assemblies 92, 94 and a core component 96. The endplate assembly 92 may include an exterior surface 98 and an interior surface 100. In this embodiment, the interior surface 100 may be relatively concave and smooth and may have a mirror surface finish. The endplate assembly 94 may have an exterior surface 104 and an interior surface 106. The surface 106 may be relatively concave and smooth and may include a mirror surface finish. In this embodiment, the exterior surfaces 98 and 104 are relatively parallel, but in other embodiments, as described above, the surfaces may be angled with respect to each other to accommodate a particular lordotic or kyphotic angle.

The core component 96 may include a flexible body 108 having end surfaces 110 and 112. As shown in FIG. 21, the core component 96 may have a generally circular cross-section as viewed from a plane perpendicular to a longitudinal axis 44. Alternate cross-sectional shapes may be desirable, and in a single core component 96, the cross sectional shape may vary depending upon the location of the perpendicular plane. In this embodiment, the end surfaces 110 and 112 may be relatively convex. The end surfaces 110, 112 may be integral with the flexible body 118 or may be mechanically or adhesively attached to the flexible body 118. For example, a coupling mechanism 114, such as a ridge, formed on the flexible body 108 may engage a coupling mechanism 116, such as a groove, on the end surface 112.

The endplate assemblies 92, 94 may be formed of the same or similar materials as endplate assemblies 22, 24 respectively, including the same or similar features or coatings. Likewise, the core component 96 may be formed from the same materials and may include the same wear resistant properties as described above for core component 26. The prosthesis 90; endplate assemblies 92, 94; and the core component 96 may be shaped as described above in FIGS. 6-18.

As shown in FIG. 20, the prosthesis 90 may be assembled by positioning end surfaces 110, 112 in contact with the interior surfaces 100, 106 respectively. The assembled prosthesis 90 may be implanted into the vertebral column 10 (FIG. 1) in the void created by the removed disc 12 such that the exterior surface 98 engages an endplate of the vertebral body 14 and the exterior surface 104 engages an endplate of the vertebral body 16.

In operation, the prosthesis 90 may elastically deform under compressive loads parallel to the longitudinal axis 44. The prosthesis 90 may also deform or flex under flexion-extension or lateral bending motion. The core component 96 may also flex to permit anterior-posterior or lateral translational displacement. The core component 96 may allow a variable center of rotation to permit flexion-extension and lateral bending motions. The flexible nature of the core component 96 may also reduce wear caused by cross-shearing or by articulation in flexion-extension and lateral bending motions. Further, as the interface between the end surfaces 110, 112 and the interior surfaces 100, 106, respectively may be unconstrained, the core component 96 may rotate about the longitudinal axis 44. The end plate assemblies 92, 94 may also rotate relative to one another. The concave interior surfaces 100, 106 may prevent ejection of the core component 26 while permitting rotation of the endplate assemblies 22, 24 relative to the core component.

As shown in FIGS. 22-27, a variety of alternative endplate assembly, core component, and coupling mechanism designs may limit lateral translation while permitting axial rotation. For example, referring now to FIG. 22, an intervertebral disc prosthesis 120 may be used as the prosthesis 18 of FIG. 2. The intervertebral disc prosthesis 120 includes endplate assemblies 122, 124 and a core component 126. The endplate assemblies 122, 124 may include exterior surfaces 128, 130, respectively and interior surfaces 132, 134, respectively. The interior surfaces 132, 134 may include concave and convex portions and may be smooth with a mirror surface finish. The concave and convex portions may form concentric rings on the interior surfaces. In the embodiment of FIG. 22, convex protrusions 136, 138 of the interior surfaces 132, 134 may function as coupling mechanisms. The endplate assemblies 122, 124 may be formed of the same or similar materials as endplate assemblies 22, 24, respectively, including the same or similar features or coatings.

The core component 126 may include a flexible body 140 having end surfaces 142, 144. In this embodiment, the end surfaces 142, 144 may comprise coupling mechanisms 146, 148 which may be dimples in approximately the center of the end surfaces. The core component 126 may be formed from the same materials and may include the same wear resistant properties as described above for the core component 26.

The prosthesis 120 may be assembled by positioning the end surfaces 142, 144 in contact with the interior surfaces 132, 134, respectively. Specifically, the coupling mechanisms 136, 138 of the endplate assemblies may engage the coupling mechanisms 146, 148 of the core component. The assembled prosthesis 120 may be implanted into the vertebral column 10 (FIG. 1) in the void created by the removed disc 12 such that the exterior surface 128 engages an endplate of the vertebral body 14 and the exterior surface 130 engages an endplate of the vertebral body 16.

Referring now to FIG. 23, an intervertebral disc prosthesis 150 may be used as the prosthesis 18 of FIG. 2. The intervertebral disc prosthesis 150 includes endplate assemblies 152, 154 which may be round and a core component 156. The endplate assemblies 152, 154 may include exterior surfaces 158, 160, respectively and interior surfaces 162, 164, respectively. Like the embodiment of FIG. 9, the interior surfaces 162, 164 may include concave and convex portions and may be smooth with a mirror surface finish. The concave and convex portions may form concentric rings on the interior surfaces. In this embodiment, convex ring protrusions 166, 168 of the interior surfaces 162, 164 may function as coupling mechanisms to engage coupling mechanisms 170, 172, respectively, which may be concave rings formed on end surfaces 174, 176 of the core component 156.

Figure 24:
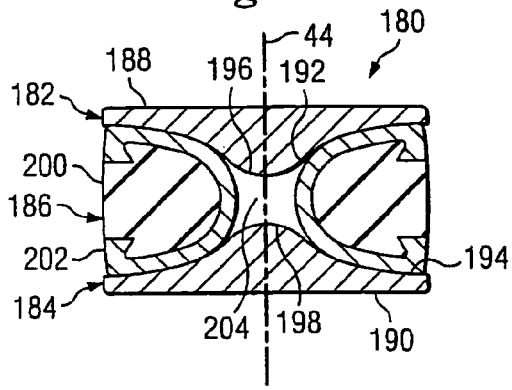

Referring now to FIG. 24, an intervertebral disc prosthesis 180 may be used as the prosthesis 18 of FIG. 2. The prosthesis 180, according to this embodiment of the present invention, includes endplate assemblies 182, 184 and a core component 186. The endplate assemblies 182, 184 may include exterior surfaces 188, 190, respectively and interior surfaces 192, 194, respectively. The interior surfaces 192, 194 may include concave and convex portions and may be smooth with a mirror surface finish. In the embodiment of FIG. 24, convex protrusions 196, 198 of the interior surfaces 192, 194 may function as coupling mechanisms. The endplate assemblies 182, 184 may be formed of the same or similar materials as endplate assemblies 22, 24, respectively, including the same or similar features or coatings.

The core component 186 may include a flexible body 200 having an articulating surface 202. In this embodiment, core component 186 may be ring shaped, having a center aperture 204 which may serve as a coupling mechanism. The core component 186 may be formed from the same materials and may include the same wear resistant properties as described above for the core component 26.

The prosthesis 180 may be assembled by positioning the core component 186 between the interior surfaces 190, 194, respectively. Specifically, the coupling mechanisms 196, 198 of the endplate assemblies may engage the coupling mechanisms 204 of the core component. The assembled prosthesis 180 may be implanted into the vertebral column 10 (FIG. 1) in the void created by the removed disc 12 such that the exterior surface 188 engages an endplate of the vertebral body 14 and the exterior surface 192 engages an endplate of the vertebral body 16.

In operation, the interface between the articulating surface 202 and the interior surfaces 190, 194 may permit both rotation about the longitudinal axis 44 and limited lateral translation. The prosthesis 180 may elastically deform under compressive loads parallel to the longitudinal axis 44 to absorb shock and provide a dampening effect. Both the articulating interface between the endplate assemblies 182, 184 and the core component 186 and the elasticity of the flexible body 200 may allow flexion-extension and lateral bending motions.

Figure 25:
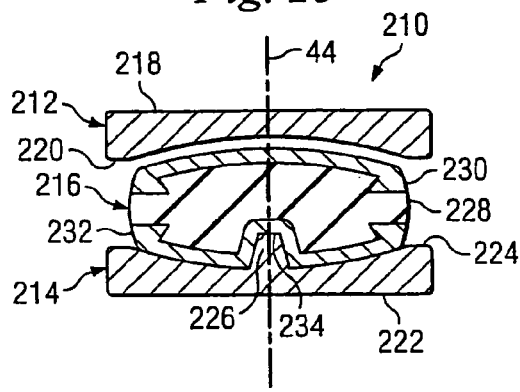

Referring now to FIG. 25, an intervertebral disc prosthesis 210 may be used as the prosthesis 18 of FIG. 2. The intervertebral disc prosthesis 210, according to this embodiment of the present invention, includes endplate assemblies 212, 214 and a core component 216. The endplate assembly 212 may include an exterior surface 218 and an interior surface 220. In the embodiment of FIG. 25, the interior surface 220 may be relatively concave and smooth and may have a mirror surface finish.

The endplate assembly 214 may have an exterior surface 222 and an interior surface 224. The interior surface 224 may be relatively concave and may include a coupling mechanism 226 which may be a protruding post.

The core component 216 may include a flexible layer 228 and outer articulating layers 230, 232 attached to the flexible layer 228. The articulating layer 230 may be convex. The articulating layer 232 may be generally convex and may include a recess 234 which may serve as coupling mechanism. In an alternative embodiment, the recess may be formed on the articulating layer 230.

The endplate assemblies 212, 214 may be formed of the same or similar materials as endplate assemblies 22, 24 respectively, including the same or similar features or coatings and therefore will not be described in further detail. The flexible layer 228 may be formed from the same flexible or elastic materials as described above for core component 26. The articulating layers 230, 232 may be formed from the same or similar materials as endplate assemblies 22, 24. Alternatively, the articulating layers 230, 232 may be formed from the same or similar materials as described above for core component 26 with modifications such as cross-linking or ion implantation to enhance wear resistance.

As shown in FIG. 25, the prosthesis 210 may be assembled by engaging the concave interior surface 220 of the endplate assembly 212 with the convex articulating layer 220 of the core component 216. The articulating layer 232 may engage the interior surface 224 of the endplate assembly 214 with the coupling mechanism 234 engaging the coupling mechanism 226.

In operation, the interface between the convex articulating layer 230 and the concave surface 220 of the endplate assembly 212, may permit both rotation about the longitudinal axis 44 and limited lateral translation. The articulating layer 232 may be permitted to rotate about coupling mechanism 226 of the interior surface 224 while permitting little or no lateral translation between the core component 216 and the endplate assembly 214. The prosthesis 210 may elastically deform under compressive loads parallel to the longitudinal axis 44 to absorb shock and provide a dampening effect. Both the articulating interface between the endplate assembly 212 and the core component 216 and the elasticity of the flexible layer 228 may allow flexion-extension, lateral bending, or axial rotation motion about the longitudinal axis 44.

Figure 26:
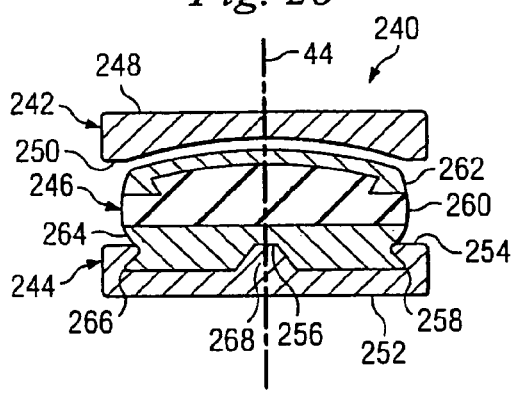

Referring now to FIG. 26, an intervertebral disc prosthesis 240 may be used as the prosthesis 18 of FIG. 2. The intervertebral disc prosthesis 240, according to this embodiment of the present invention, includes endplate assemblies 242, 244 and a core component 246. The endplate assembly 242 may include an exterior surface 248 and an interior surface 250. In the embodiment of FIG. 26, the interior surface 250 may be relatively concave and smooth and may have a mirror surface finish.

The endplate assembly 244 may have an exterior surface 252 and an interior surface 254. The interior surface 254 may be relatively flat and may include a coupling mechanism 256 which may be a protrusion and a coupling mechanism 258 which may be a groove.

The core component 246 may include a flexible layer 260 and outer articulating layers 262, 264 attached to the flexible layer 260. The articulating layer 262 may be convex. The articulating layer 264 may be relatively flat and may include a ridge 266 and an indention 268, both of which may serve as coupling mechanisms.

The endplate assemblies C2, C4 may be formed of the same or similar materials as endplate assemblies 22, 24 respectively, including the same or similar features or coatings and therefore will not be described in further detail. The flexible layer 260 may be formed from the same flexible or elastic materials as described above for core component 26. The articulating layers 262, 264 may be formed from the same or similar materials as endplate assemblies 22, 24. Alternatively, the articulating layers 262, 264 may be formed from the same or similar materials as described above for core component 26 with modifications such as cross-linking or ion implantation to enhance wear resistance.

As shown in FIG. 26, the prosthesis 240 may be assembled by engaging the concave interior surface 250 of the endplate assembly 242 with the convex articulating layer 262 of the core component 246. The articulating layer 264 may engage the interior surface 254 of the endplate assembly 244 with the coupling mechanisms 266, 268 engaging the coupling mechanisms 258, 256 respectively.

In operation, the interface between the convex articulating layer 262 and the concave surface 250 of the endplate assembly 242, may permit both rotation about the longitudinal axis 44 and limited lateral translation. The articulating layer 264 may be permitted to rotate about the axis 44 relative to the interior surface 254 or alternatively, the interface may be mechanically or adhesively fixed to prevent rotation. The prosthesis 240 may elastically deform under compressive loads parallel to the longitudinal axis 44 to absorb shock and provide a dampening effect. Both the articulating interface between the endplate assembly 242 and the core component 246 and the elasticity of the flexible layer 260 may allow flexion-extension, lateral bending, or axial rotation motion about the longitudinal axis 44.

Figure 27:
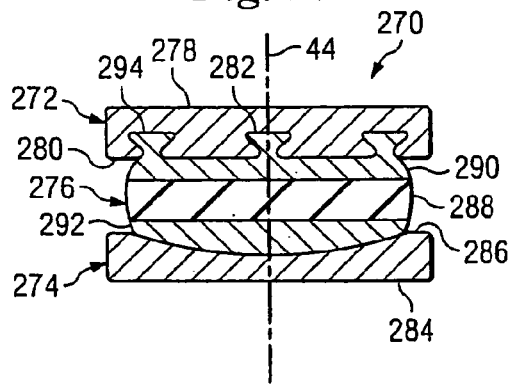

Referring now to FIG. 27, an intervertebral disc prosthesis 270 may be used as the prosthesis 18 of FIG. 2. The intervertebral disc prosthesis 270, according to this embodiment of the present invention, includes endplate assemblies 272, 274 and a core component 276. The endplate assembly 272 may include an exterior surface 278 and an interior surface 280. In the embodiment of FIG. 27, the interior surface 280 may include coupling mechanisms 282 which may concentric circular, dove tail shaped grooves.

The endplate assembly 274 may have an exterior surface 284 and an interior surface 286. The interior surface 286 may be relatively smooth and concave and may have a mirror surface finish.

The core component 276 may include a flexible layer 288 and outer articulating layers 290, 292 attached to the flexible layer 290. The articulating layer 292 may be convex. The articulating layer 290 may include flat portions and may also include coupling mechanisms 294 which may be concentric circular, dove tail shaped projections.

The endplate assemblies 272, 274 may be formed of the same or similar materials as endplate assemblies 22, 24 respectively, including the same or similar features or coatings. The flexible layer 288 may be formed from the same flexible or elastic materials as described above for core component 26. The articulating layers 290, 292 may be formed from the same or similar materials as endplate assemblies 22, 24. Alternatively, the articulating layers 290, 292 may be formed from the same or similar materials as described above for core component 26 with modifications such as cross-linking or ion implantation to enhance wear resistance.

As shown in FIG. 27, the prosthesis 270 may be assembled by engaging the concave interior surface 286 of the endplate assembly 274 with the convex articulating layer 292 of the core component 276. The articulating layer 290 may engage the interior surface 280 of the endplate assembly 272 with the coupling mechanisms 282 engaging the coupling mechanisms 294.

In operation, the interface between the convex articulating layer 292 and the concave surface 286 of the endplate assembly 274, may permit both rotation about the longitudinal axis 44 and limited lateral translation. The articulating layer 290 may permit rotation about the axis 44 relative to the interior surface 280 while the coupling mechanisms 282, 294 prevent or limit lateral motion. The prosthesis 270 may elastically deform under compressive loads parallel to the longitudinal axis 44 to absorb shock and provide a dampening effect. Both the articulating interface between the endplate assembly 274 and the core component 276 and the elasticity of the flexible layer 288 may allow flexion-extension, lateral bending, or axial rotation motion about the longitudinal axis 44. In an alternative embodiment, coupling mechanisms such as those used for 282, 294 may be used at the interface between the endplate assembly 274 and the core component 276. In this alternative, lateral translation may be prevented or limited while still allowing rotation about the axis 44. The flexibility of the core component in this alternative embodiment could still enable flexion-extension and lateral bending motion.

Figure 28:
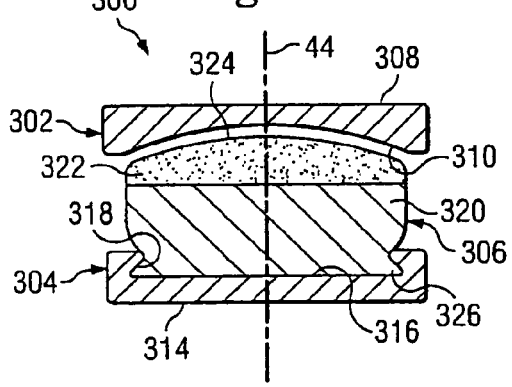

Referring now to FIG. 28, an intervertebral disc prosthesis 300 may be used as the prosthesis 18 of FIG. 2. The intervertebral disc prosthesis 300, according to another embodiment of the present invention, includes endplate assemblies 302, 304 and a core component 306. The endplate assembly 302 may include an exterior surface 308 and an interior surface 310. In the embodiment of FIG. 28, the interior surface 310 may be relatively concave and smooth and may have a mirror surface finish.

The endplate assembly 304 may have an exterior surface 314 and an interior surface 316. The interior surface 316 may be relatively flat and may include a coupling mechanism 318 which may be a groove. The exterior surfaces 308 and 314 may be relatively parallel or may be angled with respect to each other to accommodate a particular lordotic or kyphotic angle.

The core component 306 may include a flexible layer 320 and an articulating layer 322 attached to the flexible layer 320. The articulating layer 322 may have a convex surface 324. The flexible layer 320 may include a coupling mechanism 326 which may be a ridge. The core component 306 may have a generally circular cross-section as viewed from a plane perpendicular to a longitudinal axis 44. Alternate cross-sectional shapes may be desirable, and in a single core component 306, the cross sectional shape may vary depending upon the location of the perpendicular plane.

The endplate assemblies 302, 304 may be formed of the same or similar materials as endplate assemblies 22, 24 respectively, including the same or similar features or coatings and therefore will not be described in further detail. The flexible layer 320 may be formed from the same flexible or elastic materials as described above for core component 26. The articulating layer 322 may be formed from the same or similar materials as endplate assemblies 22, 24. Alternatively, the articulating layer 322 may be formed from the same or similar materials as described above for core component 26 with modifications such as cross-linking or ion implantation to enhance wear resistance.

As shown in FIG. 28, the prosthesis 300 may be assembled by mechanically or adhesively attaching the flexible layer 320 to the interior surface 316 of the endplate assembly 304. The coupling mechanism 318 may engage the coupling mechanism 326, providing mechanical attachment. Additionally or alternatively, an adhesive may be used to attached the flexible layer 320 and the interior surface 316. The convex surface 324 of the articulating layer 322 may be positioned on the concave interior surface 310. The assembled components 302-306 may be implanted into the vertebral column 10 (FIG. 1) in the void created by the removed disc 12 such that the exterior surface 308 engages an endplate of the vertebral body 14 and the exterior surface 314 engages an endplate of the vertebral body 16.

In operation, the convex surface 324 of the articulating layer 322 may articulate with the concave surface 310 of the endplate assembly 92. The prosthesis 300 may elastically deform under compressive loads parallel to the longitudinal axis 44 to absorb shock and provide a dampening effect. Both the articulating interface between the endplate assembly 302 and the core component 306 and the elasticity of the flexible layer 320 may allow flexion-extension, lateral bending, or axial rotation motion about the longitudinal axis 44. The end plate assemblies 302, 304 may also rotate relative to one another.

Figure 29:
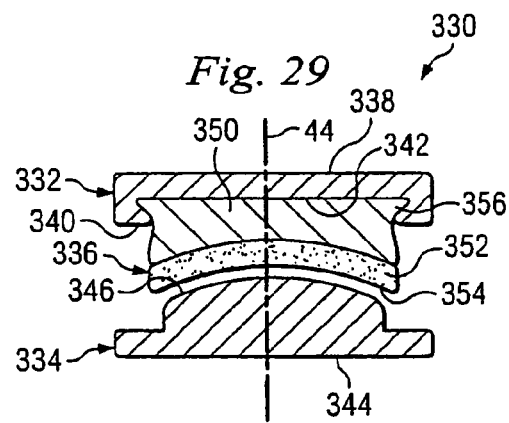

Referring now to FIG. 29, an intervertebral disc prosthesis 330 may be used as the prosthesis 18 of FIG. 2. The intervertebral disc prosthesis 330, according to another embodiment of the present invention, includes endplate assemblies 332, 334 and a core component 336. The endplate assembly 332 may include an exterior surface 338 and an interior surface 340. In the embodiment of FIG. 16, the interior surface 340 may be relatively flat and may include a coupling mechanism 342 which may be a groove.

The endplate assembly 334 may have an exterior surface 344 and an interior surface 346. The interior surface 346 may be at least partially convex and may be smooth with a mirror finish. The exterior surfaces 338 and 344 may be relatively parallel or may be angled with respect to each other to accommodate a particular lordotic or kyphotic angle.

The core component 336 may include a flexible layer 350 and an articulating layer 352 attached to the flexible layer 350. The articulating layer 352 may have a concave surface 354. The flexible layer 350 may include a coupling mechanism 356 which may be a ridge. The core component 336 may have a generally circular cross-section as viewed from a plane perpendicular to a longitudinal axis 44. Alternate cross-sectional shapes may be desirable, and in a single core component 336, the cross sectional shape may vary depending upon the location of the perpendicular plane.

The endplate assemblies 332, 334 may be formed of the same or similar materials as endplate assemblies 22, 24 respectively, including the same or similar features or coatings and therefore will not be described in further detail. The flexible layer 350 may be formed from the same flexible or elastic materials as described above for core component 26. The articulating layer 352 may be formed from the same or similar materials as endplate assemblies 22, 24. Alternatively, the articulating layer 352 may be formed from the same or similar materials as described above for core component 26 with modifications such as cross-linking or ion implantation to enhance wear resistance.

As shown in FIG. 29, the prosthesis 330 may be assembled by mechanically or adhesively attaching the flexible layer 350 to the interior surface 340 of the endplate assembly 332. The coupling mechanism 342 may engage the coupling mechanism 356, providing mechanical attachment. Additionally or alternatively, an adhesive may be used to attached the flexible layer 350 and the interior surface 340. The concave surface 354 of the articulating layer 352 may be positioned on the convex interior surface 346. The assembled components 332-336 may be implanted into the vertebral column 10 (FIG. 1) in the void created by the removed disc 12 such that the exterior surface 338 engages an endplate of the vertebral body 14 and the exterior surface 344 engages an endplate of the vertebral body 16.

In operation, the concave surface 354 of the articulating layer 352 may articulate with the convex surface 346 of the endplate assembly 334. The prosthesis 330 may elastically deform under compressive loads parallel to the longitudinal axis 44 to absorb shock and provide a dampening effect. Both the articulating interface between the endplate assembly 334 and the core component 336 and the elasticity of the flexible layer 350 may allow flexion-extension, lateral bending, or axial rotation motion about the longitudinal axis 44. The end plate assemblies 332, 334 may also rotate relative to one another.

Referring now to FIG. 30, an intervertebral disc prosthesis 360 may be used as the prosthesis 18 of FIG. 2. The intervertebral disc prosthesis 360, according to another embodiment of the present invention, includes endplate assemblies 362, 364, a core component 366, and a core component 367. The endplate assembly 362 may include an exterior surface 368 and an interior surface 370. In the embodiment of FIG. 30, the interior surface 370 may be relatively flat and may include a coupling mechanism 372 which may be a groove.

The endplate assembly 364 may include an exterior surface 374 and an interior surface 376. In the embodiment of FIG. 30, the interior surface 376 may be relatively flat and may include a coupling mechanism 378 which may be a groove. The exterior surfaces 368 and 374 may be relatively parallel or may be angled with respect to each other to accommodate a particular lordotic or kyphotic angle.

The core component 366 may include a flexible layer 380 and an articulating layer 382 attached to the flexible layer 380. The articulating layer 382 may have a concave surface 384. The flexible layer 380 may include a coupling mechanism 386 which may be a ridge. The core component 366 may have a generally circular cross-section as viewed from a plane perpendicular to a longitudinal axis 44. Alternate cross-sectional shapes may be desirable, and in a single core component 366, the cross sectional shape may vary depending upon the location of the perpendicular plane.

The core component 367 may include a flexible layer 388 and an articulating layer 390 attached to the flexible layer 388. The articulating layer 390 may have a convex surface 392. The flexible layer 388 may include a coupling mechanism 394 which may be a ridge. The core component 367 may have a generally circular cross-section as viewed from a plane perpendicular to a longitudinal axis 44. Alternate cross-sectional shapes may be desirable, and in a single core component 367, the cross sectional shape may vary depending upon the location of the perpendicular plane.

The endplate assemblies 362, 364 may be formed of the same or similar materials as endplate assemblies 22, 24 respectively, including the same or similar features or coatings and therefore will not be described in further detail. The flexible layers 380, 388 may be formed from the same flexible or elastic materials as described above for core component 26. The articulating layers 382, 390 may be formed from the same or similar materials as endplate assemblies 22, 24. Alternatively, the articulating layers 382, 390 may be formed from the same or similar materials as described above for core component 26 with modifications such as cross-linking or ion implantation to enhance wear resistance.

As shown in FIG. 30, the prosthesis 360 may be assembled by mechanically or adhesively attaching the flexible layer 380 to the interior surface 370 of the endplate assembly 362. The coupling mechanism 372 may engage the coupling mechanism 386, providing mechanical attachment. Additionally or alternatively, an adhesive may be used to attached the flexible layer 380 and the interior surface 370. The flexible layer 388 may be mechanically and/or adhesively attached to the interior surface 376 of the endplate assembly 364. The coupling mechanism 378 may engage the coupling mechanism 394, providing mechanical attachment. Additionally or alternatively, an adhesive may be used to attached the flexible layer 388 and the interior surface 376. The concave surface 384 of the articulating layer 382 may be positioned on the convex articulating surface 392. The assembled components may be implanted into the vertebral column 10 (FIG. 1) in the void created by the removed disc 12 such that the exterior surface 368 engages an endplate of the vertebral body 14 and the exterior surface 374 engages an endplate of the vertebral body 16.

In operation, the concave surface 384 of the articulating layer 382 may articulate with the convex surface 392 of the articulating layer 390. The prosthesis 360 may elastically deform under compressive loads parallel to the longitudinal axis 44 to absorb shock and provide a dampening effect. Both the articulating interface between the core component 366 and the core component 367 and the elasticity of the flexible layers 380, 388 may allow flexion-extension, lateral bending, or axial rotation motion about the longitudinal axis 44. The end plate assemblies 362, 364 may also rotate relative to one another.

Referring now to FIG. 31-32, an intervertebral disc prosthesis 400 may be used as the prosthesis 18 of FIG. 2. The intervertebral disc prosthesis 400, according to this embodiment of the present invention, includes endplate assemblies 402, 404 and a core component 406. The endplate assembly 402 may include an exterior surface 408 and an interior surface 410. In the embodiment of FIG. 31, the interior surface 410 may include a relatively concave portion which may be smooth with a mirror surface finish. The endplate assembly 404 may have an exterior surface 412 and an interior surface 414. The interior surface 414 may include a relatively concave portion. Coupling mechanisms 416 which may be bumpers may protrude from the interior surfaces 410, 414.

The core component 406 may include a flexible layer 418 and outer articulating layers 420, 422 attached to the flexible layer 418. The articulating layers 420, 422 may include coupling mechanisms 424 which may be grooves. One or more tethers 426 may extend between endplate assemblies 402 and 404.

The endplate assemblies 402, 404 may be formed of the same or similar materials as endplate assemblies 22, 24 respectively, including the same or similar features or coatings and therefore will not be described in further detail. The flexible layer 418 may be formed from the same flexible or elastic materials as described above for core component 26. The articulating layers 420, 422 may be formed from the same or similar materials as endplate assemblies 22, 24. Alternatively, the articulating layers 420, 422 may be formed from the same or similar materials as described above for core component 26 with modifications such as cross-linking or ion implantation to enhance wear resistance. The tethers 426 may be either elastic or inelastic. They may be formed, for example, of reinforcing materials such as wire, cable, cord, bands, tape, or sheets. They may be formed of any of the materials described above for endplate assemblies 22, 24 or core component 26, such as UHMWPE. In some embodiments, the tethers 426 may be braided, knitted, or woven.

As shown in FIG. 31, the prosthesis 400 may be assembled by positioning the core component 406 between the interior surfaces 410, 414 of the endplate assemblies 402, 404. The bumpers 416 may be positioned to travel along the grooves 424 of the articulating layers 420, 422. Some embodiments may have between two and four bumper/groove interfaces. The one or more tethers 26 may extend between the endplate assemblies 402, 404 to provide additional stability and/or to provide additional constraint to the prosthesis 400 when subjected to flexion/extension, lateral bending or axial rotation forces. As shown in FIG. 31, the tethers 426 may extend between the endplate assemblies 402, 404 without passing through the core component 406. The assembled prosthesis 400 may be positioned within the vertebral column 10 between the vertebrae 14, 16.

Referring again to FIG. 31-32, in operation, the bumpers 416 may travel along the grooves 424 of the articulating layers 420, 422 permitting limited rotation about the longitudinal axis 44. The rotation may be limited by the length of the grooves 424 compared to the length of the bumpers 416. For example, bumpers 416 that are nearly the same length as the grooves 424 will permit little or no rotation. In some embodiments, between one and twenty degrees of rotation may be permissible. Some embodiments may limit rotation to between three and ten degrees. The tethers 426 may also constrain the prosthesis 400 during flexion/extension, lateral bending and/or axial rotation movement. Within the constraints of the assembly, the prosthesis 400 may elastically deform under compressive loads parallel to the longitudinal axis 44 to absorb shock and provide a dampening effect. Both the articulating interfaces between the endplate assembly 402, 404 and the core component 406 and the elasticity of the flexible layer 418 may allow flexion-extension, lateral bending, or axial rotation motion about the longitudinal axis 44.

Referring now to FIG. 33-34, an intervertebral disc prosthesis 430 may be used as the prosthesis 18 of FIG. 2. The intervertebral disc prosthesis 430, according to this embodiment of the present invention, includes endplate assemblies 432, 434 and a core component 436. The endplate assembly 432 may include an interior surface 438. In the embodiment of FIG. 33, the interior surface 438 may include a relatively concave portion which may be smooth with a mirror surface finish. The endplate assembly 434 may have an interior surface 440. The interior surface 440 may include a relatively concave portion. Coupling mechanisms 441 which may be bumpers may protrude from the interior surfaces 438, 440.

The core component 436 may include a flexible layer 442 and outer articulating layers 444, 446 attached to the flexible layer 442. The articulating layers 444, 446 may include coupling mechanisms 447 which may be grooves. One or more tethers 448 may extend between articulating layers 444, 446, through the flexible layer 442 in a diagonal direction. Additionally or alternatively, one or more tethers 449 may extend between articulating layers 444, 446, through the flexible layer 442, relatively parallel to the axis 44.

The endplate assemblies 432, 434 may be formed of the same or similar materials as endplate assemblies 22, 24 respectively, including the same or similar features or coatings and therefore will not be described in further detail. The flexible layer 442 may be formed from the same flexible or elastic materials as described above for core component 26. The articulating layers 444, 446 may be formed from the same or similar materials as endplate assemblies 22, 24. Alternatively, the articulating layers 444, 446 may be formed from the same or similar materials as described above for core component 26 with modifications such as cross-linking or ion implantation to enhance wear resistance. The tethers 448, 449 may be either elastic or inelastic. They may be formed, for example, of reinforcing materials such as wire, cable, cord, bands, tape, or sheets. They may be formed of any of the materials described above for endplate assemblies 22, 24 or core component 26, such as UHMWPE. In some embodiments, the tethers 448, 449 may be braided, knitted, or woven.

As shown in FIG. 33, the prosthesis 430 may be assembled by positioning the core component 436 between the interior surfaces 438, 440 of the endplate assemblies 432, 434. The bumpers 441 may be positioned to travel along the grooves 447 of the articulating layers 444, 446. Some embodiments may have between two and four bumper/groove interfaces.

The one or more tethers 448, 449 may extend between the articulating layers 444, 446 to provide additional stability and/or to provide additional constraint to the prosthesis 430 when subjected to flexion/extension, lateral bending or axial rotation forces. The assembled prosthesis 430 may be positioned within the vertebral column 10 between the vertebrae 14, 16.

In operation, the bumpers 441 may travel along the grooves 447 of the articulating layers 444, 446 permitting limited rotation about the longitudinal axis 44. The rotation may be limited by the length of the grooves 447 compared to the length of the bumpers 441. For example, bumpers 441 that are nearly the same length as the grooves 447 will permit little or no rotation. In some embodiments, between one and twenty degrees of rotation may be permissible. Some embodiments may limit rotation to between three and ten degrees. The tethers 448, 449 may also constrain the prosthesis 430 during flexion/extension, lateral bending and/or axial rotation movement. For example, tethers 448 arranged diagonally may reinforce the flexible layer 442 against torsional shear when the groove 447 impacts the bumper 441. The tethers 449 may reinforce the flexible layer 442 against lateral shear. The tethers 448, 449 may be used alone or in combination with each other. Within the constraints of the assembly, the prosthesis 430 may elastically deform under compressive loads parallel to the longitudinal axis 44 to absorb shock and provide a dampening effect. Both the articulating interfaces between the endplate assembly 432, 434 and the core component 436 and the elasticity of the flexible layer 442 may allow flexion-extension, lateral bending, or axial rotation motion about the longitudinal axis 44.

Referring now to FIGS. 35-36, an intervertebral disc prosthesis 450 may be used as the prosthesis 18 of FIG. 2. The prosthesis 450 may include endplate assemblies 452, 454 and core component 456 and may include any of the structures of the prostheses described above. The core component 456 may include a flexible layer 458 which may include one or more modification elements 460. The flexible layer 458 may be formed from the same flexible or elastic materials as described above for core component 26.

As shown in FIGS. 35-36, prosthesis 450 includes two kidney shaped modification elements 460 as viewed from the top cross-sectional view of FIG. 36. This prosthesis 450 may be implanted such that one of the modification elements 460 is in an anterior position and one is in a posterior position to promote or restrict extension and/or flexion motion. Alternatively, the prosthesis 450 may be rotated and implanted such that modification elements 460 are laterally positioned, promoting or restricting lateral bending.

As shown in FIGS. 37-38, a prosthesis 470 may include a core component 472 having a single modification element 474. In this embodiment, the single modification element 474 may be located near the center of the core component 472 causing the center area of the core component to exhibit a different degree of rigidity than the circumferential area of the core component. The single modification element 474 may be formed in any geometry including a sphere or an ellipsoid. The modification element 474 may have rounded edges to resist wear. As shown in FIGS. 39-40, a prosthesis 490 may include a core component 492 having a single modification element 494. In this embodiment, the modification element 494 may be a ring-shaped area within the core component 492.

As shown in FIGS. 41-42, a prosthesis 50 may include a core component 512 having a plurality of modification elements 514 dispersed throughout the core component.

The modification element 460, 474, 494, 514 may be material and/or a void which controls, adjusts, or modifies the hardness, stiffness, flexibility, or compliance of the adjacent flexible layer. The modification element 460, 474, 494, 514 may be of any size, shape, or material to permit variation in the rigidity of the core component 456, 472, 492, 512 respectively. For example, certain areas of the core component 456, 472, 492, 512 may be provided with modification element 460, 474, 494, 514, respectively to provide differential stiffness between the modified areas and the non-modified areas. A variety of modification element configurations may be used to alter the rigidity of the core component, just a few examples of which are described above. The modification element may be a discrete body within the flexible layer or may have a gradient quality which may allow the modification element to blend into the flexible layer, for example, in a radial direction.

The modification elements 460, 474, 494, and 514 may be formed from materials different than the flexible layers 458, 472, 492, and 512 respectively, including any of the materials described above for the endplate assemblies 22, 24 or the core component 26. The materials may be stiffer or more pliable than the material of the flexible layer. The modification element 460, 474, 494, and 514 may be a void, and in some embodiments, one or more voids may function as reservoirs for therapeutic agents such as analgesics, anti-inflammatory substances, growth factors, antibiotics, steroids, pain medications, or combinations of agents. Growth factors may comprise any member of the families of transforming growth factor beta (TGF-beta), bone morphogenic proteins (BMPs), recombinant human bone morphogenic proteins (rh BMPs), insulin-like growth factors, platelet-derived growth factors, fibroblast growth factors, or any other growth factors that help promote tissue repair of surrounding tissues.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. An intervertebral disc prosthesis for implantation between first and second vertebral endplates, the prosthesis comprising:
   a first endplate assembly for engaging the first vertebral endplate, the first endplate assembly having a concave first inner surface and having a first outer edge with a lip extending partially downward past the first inner surface;
   a second endplate assembly for engaging the second vertebral endplate, the second endplate assembly having a concave second inner surface and having a second outer edge with a lip extending partially upward past the second inner surface; and
   a core component extending between the first and second inner surfaces and adapted to move relative to the concave first and second inner surfaces, wherein the core component includes,
      a flexible body fixedly attached between first and second end surfaces having convexly curved outer surfaces configured to mate with and engage the concave first and second inner surfaces and having respective first and second outer edges, the end surfaces being discrete from one another, wherein the flexible body includes a convexly curved outer wall and the first and second end surfaces have outer perimeters that do not extend past the outer wall and wherein the first end surface of the core component includes a peripheral groove shaped to receive and interlockingly connect with a peripheral ridge formed in the flexible body of the core component and wherein the first and second end surfaces have a hardness greater than the flexible body; and the flexible body includes a first continuous straight surface that faces outward towards and contacts the first end surface and an opposing second continuous straight surface that faces outward towards and contacts the second end surface wherein the first outer edge of the first endplate assembly extends past and below and at least partially engages the first outer edge of the first end surface and the second outer edge of the second endplate assembly extends past and up and at least partially engages the second outer edge of the second end surface.

2. The intervertebral disc prosthesis of claim 1 wherein the core component include a flexible peripheral surface integrally formed with the flexible body, wherein the flexible peripheral surface extends between the first and second end surfaces.

3. The intervertebral disc prosthesis of claim 2 wherein the flexible peripheral surface is adapted to flex, permitting movement of the first end surface relative to the second end surface.

4. The intervertebral disc prosthesis of claim 1 wherein the first endplate assembly has a circular shape.

5. The intervertebral disc prosthesis of claim 1 wherein the first end surface is adhesively affixed to the flexible body.

6. The intervertebral disc prosthesis of claim 1 wherein the first end surface comprises a ceramic.

7. The intervertebral disc prosthesis of claim 1 wherein the first end surface comprises a metal.

8. The intervertebral disc prosthesis of claim 1 wherein the first end surface comprises a rigid polymer.

9. The intervertebral disc prosthesis of claim 1 wherein the first end surface comprises a PEEK composite.

10. The intervertebral disc prosthesis of claim 1 wherein the first end surface comprises a carbon reinforced polymer.

11. The intervertebral disc prosthesis of claim 1 wherein the flexible body comprises a resilient material and the first end surface is formed of the resilient material modified by cross-linking.

12. The intervertebral disc prosthesis of claim 1 wherein the flexible body comprises a resilient material and the first end surface comprises the resilient material modified by metal ion implantation.

13. The intervertebral disc prosthesis of claim 1 wherein the flexible body comprises a polyurethane.

14. The intervertebral disc prosthesis of claim 1 wherein the flexible body comprises silicone.

15. The intervertebral disc prosthesis of claim 1 wherein the flexible body comprises a hydrogel.

16. The intervertebral disc prosthesis of claim 1 wherein the flexible body comprises copolymers of silicone and polyurethane.

17. An intervertebral disc prosthesis comprising:
a first endplate assembly having a concave inner surface and having a first outer edge with a lip extending partially downward past the first inner surface;
a second endplate assembly having a concave inner surface and having a second outer edge with a lip extending partially upward past the second inner surface; and
a core component including convex outer portions having convexly curved outer surfaces configured to mate with and engage the concave first and second inner surfaces and having respective first and second outer edges, discrete from one another and adapted to articulate with the concave inner surfaces of the first and second endplate assemblies and further including a monolithic non-annular flexible portion separating and fastened to the outer portions, wherein the flexible portion is more resilient than the outer portions and includes a convexly curved outer wall wherein the convex outer portions have outer perimeters that do not extend past the outer wall of the flexible portion, and wherein at least one of the outer portions of the core component and the flexible portion of the core component are fixedly attached and interconnectingly fastened together with a peripherally extending ridge of the flexible portion received within a peripherally extending groove of the at least one outer portion;
the outer portions each including flat inner surfaces that face towards and contact the flexible portion, the flat inner surfaces being perpendicular to a longitudinal axis that extends through the endplate assemblies and the core component, wherein the first outer edge of the first endplate assembly extends past and below and at least partially engages the first outer edge of the first end surface and the second outer edge of the second endplate assembly extends past and up and at least partially engages the second outer edge of the second end surface.

18. The intervertebral disc prosthesis of claim 17 wherein the flexible portion is fastened to the outer portions with an adhesive.

19. The intervertebral disc prosthesis of claim 17 wherein at least one of the outer portions comprises ultra-high molecular weight polyethylene (UHMWPE).

20. The intervertebral disc prosthesis of claim 17 wherein at least one of the outer portions comprises a cobalt-chrome alloy.

21. The intervertebral disc prosthesis of claim 17 wherein at least one of the outer portions comprises polyetheretherketone (PEEK).

22. The intervertebral disc prosthesis of claim 17 wherein the flexible portion comprises polyurethane.

23. The intervertebral disc prosthesis of claim 17 wherein the flexible portion comprises polyolefin rubber.

24. The intervertebral disc prosthesis of claim 17 wherein the flexible portion comprises silicone.

25. The intervertebral disc prosthesis of claim 17 wherein one of the outer portions moves relative to the other outer portion under flexion-extension movement.

26. The intervertebral disc prosthesis of claim 17 wherein one of the outer portions moves relative to the other outer portion under lateral bending motion.

* * * * *